(12) United States Patent
Kundalia et al.

(10) Patent No.: US 11,348,442 B2
(45) Date of Patent: May 31, 2022

(54) HYGIENE DETECTION DEVICES AND METHODS

(71) Applicant: 12180502 Canada Inc., Mississauga (CA)

(72) Inventors: Jitan Dineshkumar Kundalia, Crawley (GB); Jordan Peter Caspersz, Toronto (CA); Gurmuk Singh Dhesi, Luton (GB); Jobin Mathew Varughese, Brampton (CA)

(73) Assignee: 12180502 Canada Inc., Mississauga (CA)

( * ) Notice: Subject to any disclaimer, the term of this patent is extended or adjusted under 35 U.S.C. 154(b) by 0 days.

(21) Appl. No.: 17/070,420

(22) Filed: Oct. 14, 2020

(65) Prior Publication Data

US 2022/0114878 A1 Apr. 14, 2022

(51) Int. Cl.
*G08B 21/24* (2006.01)
*A61B 5/00* (2006.01)
*A61B 5/11* (2006.01)

(52) U.S. Cl.
CPC .......... *G08B 21/245* (2013.01); *A61B 5/1126* (2013.01); *A61B 5/681* (2013.01); *A61B 5/742* (2013.01); *A61B 2562/0219* (2013.01)

(58) Field of Classification Search
CPC ..... G08B 21/245; A61B 5/1126; A61B 5/681; A61B 5/742
USPC ...................................................... 340/573.1
See application file for complete search history.

(56) References Cited

U.S. PATENT DOCUMENTS

| | | | |
|---|---|---|---|
| 8,698,637 B2 | 4/2014 | Raichman | |
| 10,223,894 B2 | 3/2019 | Raichman | |
| 10,607,471 B2 | 3/2020 | Hood et al. | |
| 10,692,355 B2 | 6/2020 | Waghode et al. | |
| 10,748,410 B2 | 8/2020 | Liu et al. | |
| 2011/0125063 A1 | 5/2011 | Shalon et al. | |
| 2011/0169646 A1 | 7/2011 | Raichman | |
| 2011/0206378 A1* | 8/2011 | Bolling ................ | G08B 21/245 398/108 |
| 2012/0016641 A1* | 1/2012 | Raffa .................... | G06F 1/1694 703/2 |

(Continued)

FOREIGN PATENT DOCUMENTS

WO 2020126000 6/2020

OTHER PUBLICATIONS

International Search Report & Written Opinion dated Jan. 10, 2022; WIPO Aplication No. PCT/CA2021/051412.

*Primary Examiner* — Kerri L McNally
(74) *Attorney, Agent, or Firm* — Rowand LLP

(57) ABSTRACT

A wearable device and a method of indicating a hygiene status on a wearable device. The method may include obtaining a first gesture signal using an inertial sensor in the wearable device and matching the first gesture signal to one of a plurality of gesture signal patterns stored in the wearable device and associated with a multi-stage gesture. It may further include obtaining another gesture signal and matching it to another of the plurality of gesture signal patterns. It may then include determining, based on detecting at least two of the gestures in the multi-stage gesture that the multi-stage gesture has been completed and, as a result, setting the hygiene status to a clean state. The device may output a sensory signal using an output device indicating the clean state.

20 Claims, 8 Drawing Sheets

(56) References Cited

U.S. PATENT DOCUMENTS

| | | |
|---|---|---|
| 2013/0158367 A1 | 6/2013 | Pacione et al. |
| 2014/0318699 A1 | 10/2014 | Longinotti-Buitoni et al. |
| 2014/0347491 A1 | 11/2014 | Connor |
| 2014/0349256 A1 | 11/2014 | Connor |
| 2015/0126873 A1 | 5/2015 | Connor |
| 2015/0127365 A1 | 5/2015 | Rizvi et al. |
| 2015/0254964 A1* | 9/2015 | Raichman .............. A61G 11/00 340/573.1 |
| 2016/0275778 A1* | 9/2016 | Wallace ................ G08B 21/245 |
| 2016/0314683 A1* | 10/2016 | Felch ................... G08B 21/245 |
| 2018/0357886 A1 | 12/2018 | Tavori et al. |
| 2019/0110743 A1 | 4/2019 | Contant |
| 2019/0228640 A1 | 7/2019 | Freedman et al. |
| 2020/0074835 A1 | 3/2020 | Waghode et al. |

* cited by examiner

HYGIENE DETECTION DEVICES AND METHODS

FIELD

The present disclosure relates to devices and methods for detecting hygiene and, in particular, wearable devices for detecting and signaling hygiene status of an individual.

BACKGROUND

One of the impacts of the COVID-19 pandemic has been a heighted awareness of the importance of proper hygiene protocol. This is especially so in the case of in hospitals, nursing homes, and other high risk environments, but also applies to lower risk environments where potential pathogens could be communicated or transmitted. One example is food handling situations, such as grocery stores, restaurants, etc.

There are many systems designed to monitor use of a sanitization station, such as a sink or sanitizer dispensing location. Such systems are typically designed to be installed at the sanitization station and detect usage of the station.

It would be advantageous to provide for improved methods and devices for detecting and/or indicating hygiene status.

BRIEF DESCRIPTION OF THE DRAWINGS

Embodiments will be described, by way of example only, with reference to the accompanying figures wherein.

DETAILED DESCRIPTION

Figure 1:
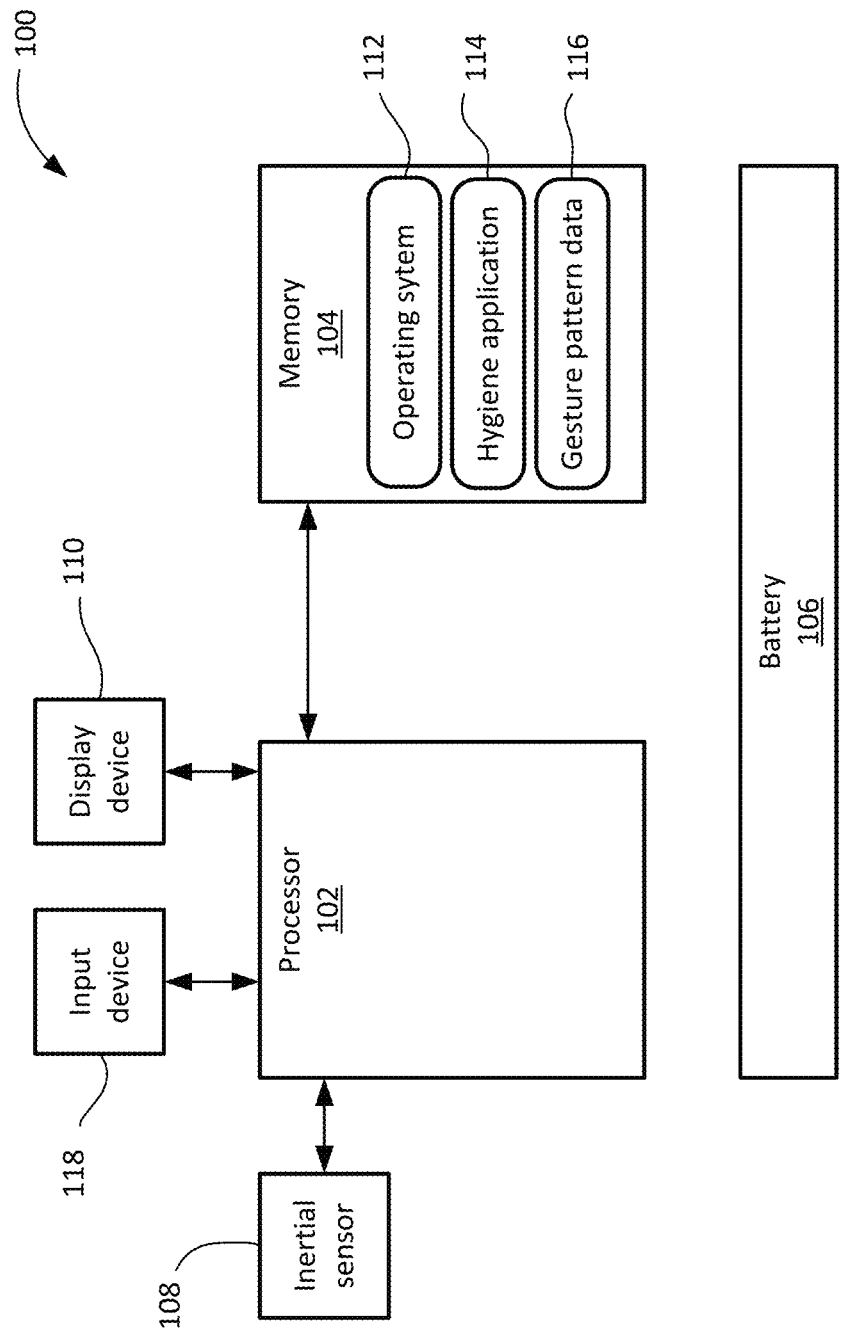
FIG. 1 is a simplified block diagram of a wearable device for indicating hygiene status of a wearer.

In one aspect, the present application describes a method of indicating a hygiene status on a wearable device. The method may include obtaining a first gesture signal using an inertial sensor in the wearable device; matching the first gesture signal to one of a plurality of gesture signal patterns stored in the wearable device and associated with a multi-stage gesture; obtaining at least one more gesture signal using the inertial sensor; matching the at least one more gesture signal to respective other ones of the plurality of gesture signal patterns; determining, based on matching the first gesture signal to the one of the plurality of gesture signal patterns plus matching the at least one more gesture signal to respective other ones of the plurality of gesture signal patterns that the multi-stage gesture has been completed and, as a result, setting the hygiene status to a clean state; and outputting a sensory signal using an output device indicating the clean state.

In some implementations, determining may be further based on determining that the first gesture signal and the at least one more gesture signal do not match an excluded gesture pattern.

In some implementations, determining that the multi-stage gesture has been completed may be further based on determining that a cumulative duration of the first gesture signal and the at least one more gesture signal is greater than a minimum total duration value.

In some implementations, the first gesture signal and each gesture signal in the at least one more gesture signal are respective gesture signals, and determining that the multi-stage gesture has been completed may be further based on determining that a respective elapsed duration of each of the respective gesture signals is greater than a respective minimum duration associated with that respective gesture signal.

In some implementations, matching the first gesture signal to one of the plurality of gesture signal patterns may include determining that the first gesture signal differs from said one of the plurality of gesture signal patterns by less than a threshold amount. In some examples, the threshold amount may be based on a standard deviation measurement associated with said one of the plurality of gesture signal patterns and stored on the wearable device.

In some implementations, the multi-stage gesture may include at least six gestures, the first gesture signal and each gesture signal in the at least one more gesture signal are respective gesture signals, and the matching the first gesture and the matching the at least one more gesture signal may include matching respective ones of the respective gesture signals to each of the at least six gestures.

In some implementations, the method may further include detecting that an elapsed time since the setting the hygiene status to the clean state exceeds an expiry time and, as a result, setting the hygiene status to unclean, and outputting a signal to indicate the unclean hygiene status. In some examples, the method may further include, prior to detecting that the elapsed time exceeds the expiry time, detecting that the elapsed time exceeds an intermediate time shorter than the expiry time and, as a result, setting the hygiene status to intermediate, outputting a signal to indicate the intermediate hygiene status.

In some implementations, the sensory signal indicating the clean status includes a green output, the signal to indicate the intermediate hygiene status includes a yellow output, and signal to indicate the unclean hygiene status includes a red output. In some of those instances, the output device may include one or more light-emitting diodes on an external surface of the wearable device, and the green output may include illuminating the one or more light-emitting diodes green, the yellow output may include illuminating the one or more light-emitting diodes yellow, and the red output may include illuminating the one or more light-emitting diodes red.

In some implementations, the method may further include, subsequent to the setting of the hygiene status to clean, obtaining a new gesture signal and matching the new gesture signal to a reset gesture pattern and, as a result, setting the hygiene status to unclean and outputting a signal indicating the unclean hygiene status.

In some implementations, the output device may include one or more of a light-emitting diode, a display screen, a speaker, or a vibrator.

In some implementations, the method may further include receiving a wireless signal from a paired wearable device, the wireless signal including at least one gesture signal obtained by the paired wearable device, and determining may further include matching the at least one gesture signal to a particular one of the plurality of gesture signal patterns. In some cases, the at least one gesture signal is obtained by the paired wearable device during a time period in which the wearable device obtains the first gesture signal, and the one of the plurality of gesture signal patterns matched to the first gesture is paired with the particular one of the plurality of gesture signal patterns matched to the at least one gesture signal.

In another aspect, the present application describes a wearable device to indicate a hygiene status. The wearable device may include a memory storing a plurality of gesture signal patterns associated with a multi-stage gesture; an inertial sensor to output gesture signals representative of movement of the device; a processor; and an output device. The memory may include processor-executable instructions that, when executed by the processor, are to cause the processor to carry out one or more of the methods described herein. In some cases, wearable device may be a bracelet, armband, wristband, wristwatch, or ring.

For illustrative purposes, specific examples will now be explained in greater detail below in conjunction with the figures.

As noted above, proper hygiene is of increasing concern in a world in which viruses and bacteria pose a significant health risk. This is particular true in certain settings in which people are particularly vulnerable to contracting bacterial or viral infections, such as within hospitals, dental suites, long term care facilities, or other settings involving exposed or vulnerable populations. It is also of increasing public importance to be reassured that proper protocols are being followed in terms of hygiene in those settings and even in less clinical settings, such in connection with food handling or preparation (e.g., waiters, cooks, grocery store employees, butchers, etc.).

One example of a key hygiene activity is proper handwashing. Handwashing in this application may refer to handwashing with soap and water or handwashing with sanitizer.

In many cases, proper hygiene technique may have a prescribed or recommended protocol for successful completion. For example, in the case of handwashing, the prescribed technique may include specific actions/gestures. In many cases, like handwashing, the prescribed technique may involve a minimum duration for the actions/gestures. In some cases, each individual action/gesture may have an associated minimum duration.

The present application proposes a wearable device to determine and indicate hygiene status of the wearer. The status may be indicated using a sensory output, e.g. visual, auditory, haptic, or a combination or sub-combination thereof. A sensory output that is, for example, visible to people in proximity to the wearer of the device may communicate the wearer's current hygiene status and may give those people confidence that the wearer has a clean status. It may also or alternatively be useful in reminding the wearer of their status and/or a change in their hygiene status. In some cases, the sensor output may serve as a reminder to the wearer to re-engage in a hygiene protocol to maintain or obtain a clean status.

The wearable device for determining and indicating hygiene status may be useful for staff working in health care, hospitality, retail, or other such environments. The wearable may, in some implementations, be configured to be attached to a user's hand or arm. For example, the wearable device may in the form of a bracelet, armband, wristwatch, wristband, ring, etc.

In some aspects, the wearable device detects a hygiene event and, in particular, a multi-stage hygiene event based on gesture recognition. For example, the wearable device may identify a hygiene event through detecting one of the two or more defined gestures associated with a multi-stage hygiene event. In some cases, to determine that the hygiene event has been validly completed, the device determines whether all, or at least a minimum number, of the gestures in the multi-stage hygiene event have been detected.

In some aspect, detecting a gesture may include matching a gesture signal from a gesture-sensing device to a stored gesture pattern. Matching may include determining that the gesture signal is within a range of difference from the pattern. The acceptable range of deviation from the pattern may be set based on a stored variation value, such as a standard deviation value. The difference may be determined based on a distance measurement between the signal and the pattern.

The pattern may be a predetermined gesture pattern stored in the wearable device. In some instances, the pattern may be predetermined during a training phase during which a wearer of the device performs the prescribed gesture a plurality of times. In one example, an averaging or weighted averaging function may be used to generate the gesture pattern from the gesture signals obtained during the training phase. The gesture pattern may begin with a prescribed pattern stored within the device that is then modified by the training phase to customize a universal prescribed pattern for that gesture to be customized to the wearer's particular performance of that gesture. In some cases, the customization may be constrained within a permissible range of difference from the universal prescribed pattern. Each gesture in a multi-stage gesture may be customized in such a manner in some implementations.

In another example, the gesture pattern is a predetermined pattern stored on the wearable device, and the training phase in which the wearer performs the prescribed gesture a plurality of times builds a training set of signals having pattern variability. The training set of signal may result in a distribution of pattern signals, which may have a roughly normal (Gaussian) distribution in some cases. Detection of a valid gesture after the training phase may be based on detecting a gesture signal that is within a certain measure of the predetermined pattern. That measure may be based on the standard deviation of the distribution of training signals. That is, the training phase may determine the standard deviation of the wearer's performance of that gesture, and that standard deviation may determine the threshold of deviation permitted for detecting a valid gesture.

In some instance, the wearable device further stores one or more excluded gesture patterns corresponding to movements that are not hygiene events. For example, in the case of handwashing the wearable device may include excluded patterns for actions such as handshaking, waving, writing, or other such activities.

Matching a gesture signal to a stored gesture pattern may include determining that the gesture signal is sufficiently matched to one of the stored gesture patterns and may include further determining that the gesture signal is sufficiently different from one of the excluded gesture patterns. In some instances, to be validly determined to be a hygiene event, the detected gesture signal may be determined to be closer to one of the stored gesture patterns that is it to one of the excluded patterns.

The wearable device may have two or more states. For example, the device may have a "clean" state and an "unclean" state. Transition from an "unclean" state to a "clean" state may be based on detecting a valid hygiene event, such as detection of a valid multi-stage hygiene gesture event that has a sufficiently long duration. "Unclean" in this context does not necessarily indicate that the wearer is contaminated or unhygienic, but rather that a valid hygiene event has not been detected or has not been detected in more than a pre-set period of time, e.g. a hygiene/cleanliness expiry time. The wearable device may have more than two states. For example, it may have a clean state, and unclean state and an intermediate or transitional or in-between state. The intermediate state may indicate that the clean hygiene status is close to expiry, i.e. will transition from clean to unclean soon if a valid hygiene event is not detected. The intermediate state may also or alternatively indicate that a partly-valid hygiene event was detected, e.g., a multi-state gesture detection that includes fewer than the minimum number of predefined gestures, or less than the prescribed duration, as examples.

Status may be indicated using one or more output devices. As an example, the wearable device may include a visual output device, such as display, or one or more LEDs. It may also or alternatively include an audio output device, such as a speaker. It may also or alternatively include a haptic output device, such as a vibrator.

In some cases hygiene status may be visually indicated using a red and green LEDs to correspond to unclean and clean states. In some case a yellow LED may be used to indicate an in-between state that will transition to unclean (red) if a hygiene event is not performed soon. In some implementations, after a set period of time a green/clean state changes to a yellow/intermediate state, and after a further period of time changes to a red/unclean state. The LEDs may be configured to blink during a time period leading up to a change in state, or for a time period after a change in state. In some cases, following an extended time in an unclean state, all the LEDs may blink, pulse, or otherwise signal that the hygiene event is long overdue. Other timings, signals, patterns may be used to signal the "decay" in cleanliness status over time. Other LEDs or visual output devices may be used for signaling hygiene state or other states of the device (e.g. charging, ready for pairing, etc.).

Advantageously, in some embodiments the wearable device may operate in an "always on" manner in which is constantly displays or outputs a signal indicating current hygiene status. In this manner, other persons in proximity to the wearer can easily ascertain the hygiene status of the wearer from the displayed signal from the wearable device. In some implementations, the wearable device may have one or more input devices through which the user may put the device into a sleep or pause or off mode. Such a mode may be advantageous for times when the wearer is not actively on duty or in a role in which he or she is supposed to wear the wearable device to display hygiene status. In some cases, the wearable device may include a "silent" mode in which the hygiene status continues to be displayed visually but other signals of hygiene status or hygiene status changes, such as vibrations or audio alerts, are not output.

Reference is now made to FIG. 1, which shows in block diagram form a simplified example of a wearable device 100 in accordance with one aspect of the present application. The device 100 includes at least one processor 102 and a memory 104. The memory 104 may include one or more computer-readable media and may include persistent memory and non-persistent memory. The memory 104 may store various processor-executable instructions, such as an operating system 112. The operating system 112 may control basic device functions, inter-process messaging, and other lower-layer operations. The operating system 112 may, in various implementations, be implemented as a monolithic operating system, a layered operating system, a virtual machine, or a kernel-based operating system. Other architectures may be used depending on the implementation.

The device 100 may include a display device 110, an input device 118, an inertial sensor 108, and a battery 106. The battery 106 may power the electronic elements within the wearable device 100. The battery 106 may include an integrated battery, a removable/replaceable battery, a rechargeable battery, or two or more such batteries. The wearable device 100 may further include battery charging circuitry (not shown) to receive charge current from, for example, a microUSB connector or other external power source. In some cases, the battery charging circuit may be coupled to a kinetic energy converter configured to convert motion of the wearable device 100 into a charge current. In some cases, the battery charging circuit may include magnetic near-field charging circuitry. In some cases, other alternative energy charging sources may be included in the battery charging circuit, such as solar.

The display device 110 may include one or more visual output devices, such as a multi-pixel display screen (e.g. LCD, LED, or OLED display) and/or one or more individual light-emitting diodes (LEDs). The LEDs may include one or more single colour LEDs, or may include one or more multi-colour LEDs.

The input device 118 may include one or more actuators for detecting or receiving user input. Example input devices 118 may include a touchscreen, a touch-sensitive bezel or other such surface, one or more buttons, wheels, dials, keys, or other such electro-mechanical actuators. The input device 118 may further include sensors for receiving auditory input, such as a microphone.

The inertial sensor 108 may include one or more of an accelerometer, a gyroscope, and a magnetometer. As an example, the inertial sensor 108 may include a tri-axis accelerometer configure to output x, y, and z-axis signals representing the sensed acceleration of the wearable device 100 in the x, y, and z-axis directions, respectively. The x, y, and z-axis signals thus represent a set of signals characterizing the motion of the wearable device 100 in three-dimensional space. In another example, the inertial sensor 108 includes a gyroscope configured to output a, b, and c signals representing tri-axis rotational rates, e.g. the rate of rotation about a corresponding coordinate axis in rad/s. In some cases, the inertial sensor 108 includes both accelerometer measurements and gyroscope measurements.

The memory 104 may store a hygiene application 114 and gesture pattern data 116. The gestures pattern data 116 may include one or more preconfigured or pre-set gesture signal patterns. In some cases, one or more of the gesture signal patterns may represent a signal pattern obtained via the inertial sensor 108 during a training phase and stored in the memory 104. The stored gesture signal pattern may include an average, weighted average, or other combination of two or more signal patterns. In some cases, each gesture signal pattern may be associated with a standard deviation value and/or a threshold value based on a standard deviation value, where the standard deviation value was determined during a training phase.

The hygiene application 114 may include processor-executable instructions that, when executed, cause the processor 102 to carry out certain functions to identify gestures and update or manage a hygiene status associated with the device 100. In particular, the hygiene application 114 may cause the processor 102 to receive one or more gesture signals from the inertial sensor 108 and to compare those one or more gesture signals to the gesture pattern data 116. For example, the application 114 may compare a gesture signal to each of the stored gesture signal patterns to identify the closest matching gesture pattern. In some cases, a threshold value, such as a standard deviation value, may be used to assess whether a gesture signal is sufficiently close to a stored gesture signal pattern to be matched. In some cases, a distance metric may be used to compare signals and calculate a distance or difference value.

The hygiene application 114 may maintain a hygiene status in memory 104. As described above the hygiene status may have at least two settings: a clean setting and an unclean setting. The hygiene application 114 may initially set the status to unclean and may change the status to clean if a valid hygiene event is detected. The valid hygiene event may be detected based on detecting gesture signal matches to one or more of the gesture signal patterns. In some cases, the valid hygiene event may further be based on detecting that the gesture(s) associated with the hygiene event are performed for at least a minimum duration, and/or that individual gestures within a multi-stage hygiene event are each performed for a respective minimum duration.

The hygiene application 114 may be configured to signal the current hygiene status and/or a change in hygiene status via the display device 110. That is, the display device 110 may visually signal the current status and/or a change in status. For example, if the display device 110 includes a display screen the current status may be displayed in text, imagery, graphics, coloured border, or in some other visual fashion. If the display device 110 includes one or more LEDs, the current status may be indicated through the colour of the illuminated LED. As an example, the LEDs (whether individual LEDs or a multi-colour LED) may be green for a "clean" status, red for an "unclean" status, and "yellow" for an intermediate status. Other devices (not shown) may also or alternatively be used to signal status or a change in status, including, for example, a speaker for audio alerts and/or a vibrator for haptic alerts.

The hygiene application 114 may cause a time to be tracked since detection of a hygiene event. The time may be used to automatically transition the wearable device 100 to an intermediate and/or an unclean status as time elapses since detection of a valid hygiene event. Accordingly, the wearer of the wearable device 100 and those persons around the wearer are notified that the time since the hygiene event has exceeded a predetermined threshold, thereby necessitating that the wearer perform a valid hygiene event so as to reset their status to clean.

For ease of discussion, the hygiene application 114 is characterized herein as an application; however, it will be appreciated that some or all of the functions or operations of the application may be implemented within the operating system 112, in separate applications, modules, sub-routines, or in another software paradigm.

It will be appreciated that the wearable device 100 may, in some embodiment, contain a number of components not specifically shown in FIG. 1. For example, in some cases, the wearable device 100 may include short-range communication circuitry, such one or more radios and antennas and associated modulation/demodulation components. Example short-range communication circuitry may include a WiFi chip in accordance with one or more IEEE 802.11 protocols, a Bluetooth™ chip, a near-field communication (NFC) chip, a radio-frequency identification (RFID) chip, or the like. In some cases, the wearable device 100 may include longer-range communication circuitry, including a cellular communication subsystem for radio communication in accordance with 3G, 4G, or 5G protocols, or any future wireless communication protocols.

Figure 2:
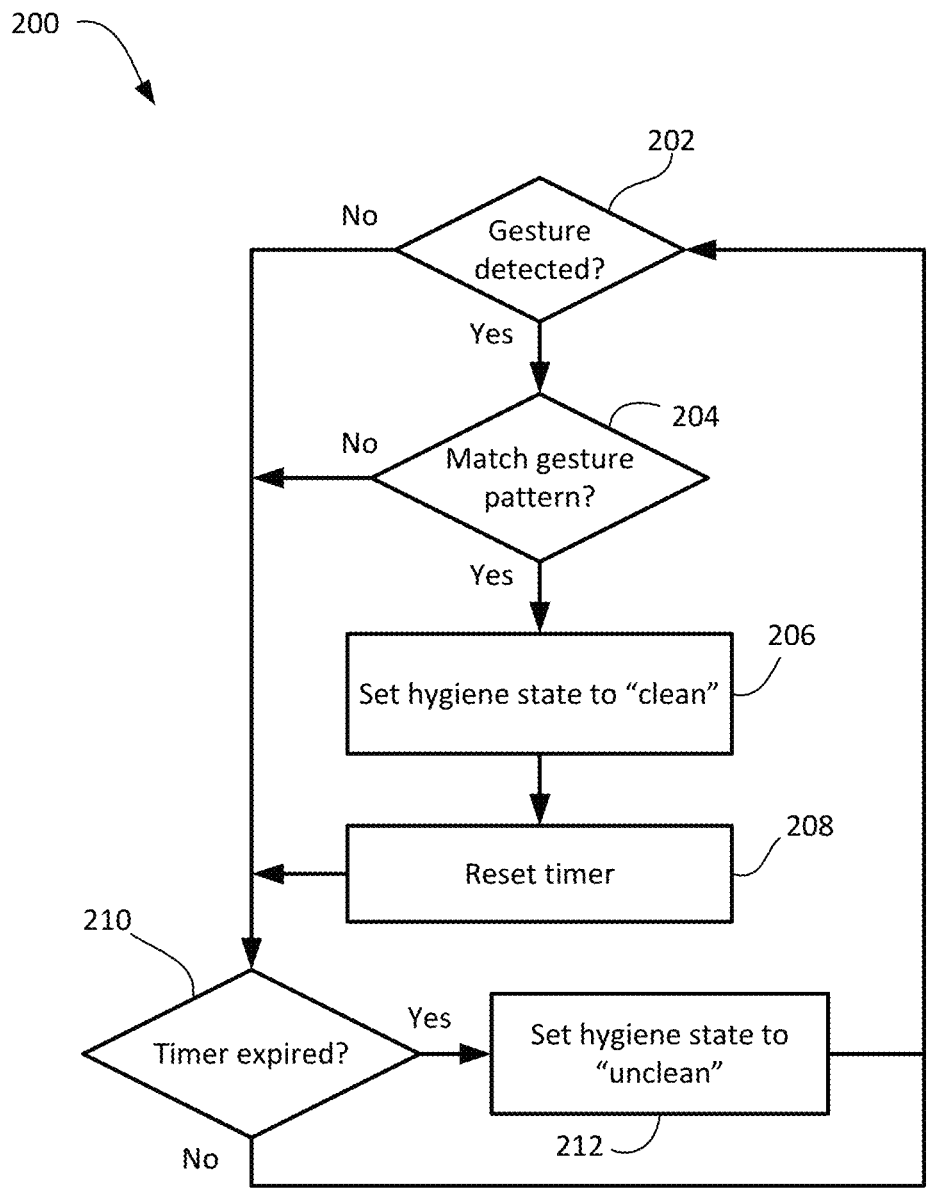
FIG. 2 is a flowchart showing one simplified example method of tracking hygiene status.

Reference is now made to FIG. 2, which shows one example method 200 of indicating a hygiene status using a wearable device. The method 200 may be implemented by way of processor-executable instructions stored on a wearable device 100 and that, when executed by one or more processors in the wearable device 100 cause the processor and associated components to carry out the described functions or operations. The instructions may be embodied in a hygiene application in some implementations, or in some other software construct.

In operation 202, the wearable device determines whether a gesture is detected. In some implementations, the wearable device may have a "wake-up" or "trigger" gesture that, when identified based on the signal(s) from the inertial sensor causes the wearable device to begin attempting to match received gesture signals to stored gesture signal patterns. The wake-up or trigger gesture may include a detected movement at a speed or intensity greater than some baseline threshold. In this manner, the device may avoid performing matching attempts based on non-significant signals form the inertial sensor when the wearable device is stationary or not in significant motion, e.g., when at rest, when typing, when or engaged in activity in which the hands/arms are relatively stationary. In such implementations, the wake-up or trigger gesture may be detection of a movement above a threshold level of movement.

In some cases, there may be no wake-up or trigger gesture and the wearable device constantly monitors the signal(s) from the inertial sensor.

If a possible gesture is detected in operation 202, e.g., a wake-up or trigger signal is identified, then in operation 204, the wearable device attempts to match the gesture signal(s) from the inertial sensor(s) to one of the stored gesture signal patterns. As mentioned above, this may include determining whether a received gesture signal is within a certain threshold of deviation or difference from the stored gesture signal. In the example of a tri-axis accelerometer, this may include determining whether all three signals deviate no more than a threshold amount from respective stored gesture signal patterns for those axes. In some cases, it may include determining that at least two of the signals deviate no more than a threshold amount from their respective stored gesture signal patterns for those axes. In some cases, it may include determining that at least one of the signals deviate no more than a threshold amount from any one of the respective stored signal patterns. In the case of a combined accelerometer and gyroscope, it may include determining that all six or some subset of the six inertial measurement signals deviate no more than a threshold amount from stored signal patterns. In some cases, the permitted deviation from the signal patterns may vary. To illustrate at least one of the signals corresponding to one of the axes may need to be within a certain lower threshold deviation from the signal pattern and, if it is, then the other signals corresponding to the other axes may need to be within a certain higher threshold deviation from their respective signal patterns. Other mechanisms for gesture recognition will be appreciated by those ordinarily skilled in the art, including techniques for evaluating a confidence metric associated with matching the gesture, combining signals relating to axes for evaluation against corresponding signal patterns, and other algorithms for detecting defined gestures using inertial sensors.

Detection of a match between a gesture signal and a gesture signal pattern may include detection of a sufficient match over at least a minimum signal duration. For example, to constitute a match to the gesture signal pattern, the gesture signal may need to sufficiently match at least a portion of the gesture signal pattern for a minimum signal duration such as 1 second, 2 seconds, etc. In other words, the wearable device may process a windowed portion of the received gesture signal having the minimum signal duration, and many attempt to match that signal to the stored signal patterns. Note, that the minimum signal duration sufficient to find a match and identify a corresponding gesture pattern may be shorter than the minimum duration of the gesture sufficient to constitute a valid gesture within the context of detecting the hygiene event, as will be discussed further below. As an example, a handwashing gesture may include a gesture involving palm-to-palm interlaced fingers reciprocating back-and-forth motion. Detection of a gesture corresponding to this motion may result from matching received inertial signals to stored signal patterns for that gesture based on a 1 second window of the received signals; whereas, for that gesture to constitute a valid performance of that gesture within the context of a handwashing operation, it may need to be performed (and detected as being performed) over a longer duration, such as ten seconds or twenty seconds.

If the gesture signal is matched to one of the stored gesture signal patterns, then in operation 206 the hygiene state of the wearable device is set to "clean". This may include illuminating an LED, or otherwise outputting a signal signifying the current clean status and/or the change in status (if any) to "clean". In operation 208, a status timer is initialized and/or reset. The status timer tracks the time since detection of the most recent hygiene event, i.e. since detection of the gesture in operation 204.

As the wearable device monitors for detection of valid hygiene gestures, it also tracks the status timer for expiry, as indicated in operation 210. That is, if an elapsed time since the most recent hygiene event exceeds an expiry time, then the wearable device sets its state to "unclean" in operation 212. This may include illuminating an LED and/or outputting another signal signifying that the current status is unclean and/or that there has been a change in status to "unclean". The status may be changed back to "clean" if the wearable device subsequently detects a valid hygiene event based on the gesture detection operations 202, 204, 206.

The foregoing simplified example method 200 illustrates operation of the gesture detection and status change operations. As noted above, in many implementations, the hygiene event may include a multi-stage gesture operation in which the hygiene event is composed of two or more prescribed distinct gestures. An example of such a hygiene event is handwashing, where the prescribed gestures include at least two different hand movements. In many handwashing protocols, there are at least six distinct gestures. While many of the illustrative examples used herein relate to handwashing, it will be appreciated that the present application may be applicable to other hygiene events involving gestures.

Figure 3:
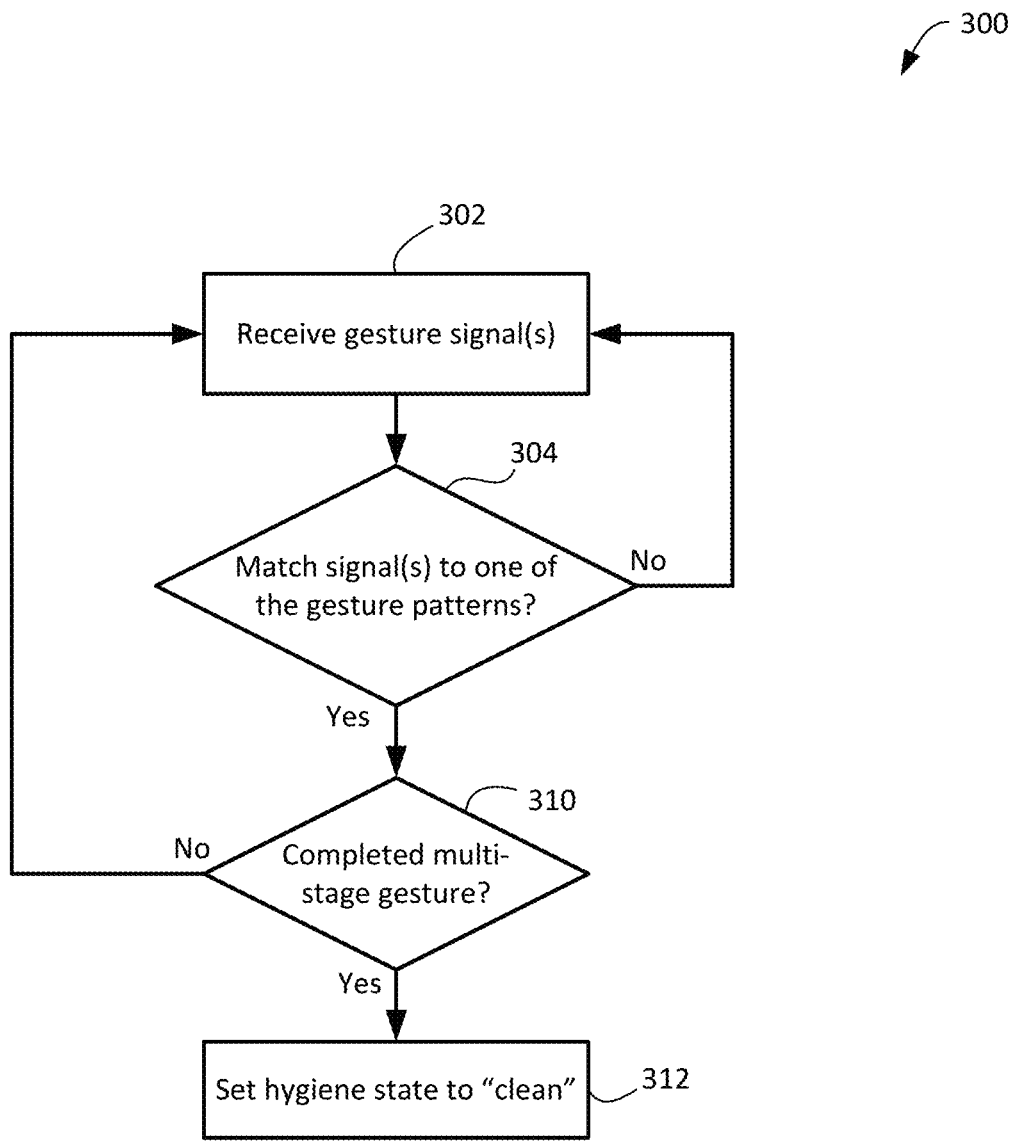
FIG. 3 is a flowchart showing an example method of detecting a multi-stage hygiene gesture.

Reference is now also made to FIG. 3, which shows, in flowchart form, an example process 300 for detecting a valid multi-stage hygiene event. The process 300 may be incorporated into the gesture detection operations 202, 204, 206 of method 200 (FIG. 2), in some examples.

The process 300 begins in operation 302, in which the device receives gesture signal(s). The gesture signal(s) may be received via one or more inertial sensors in the device, such as an accelerometer, gyroscope, and/or magnetometer. In operation 304, the wearable device determines whether the received gesture signals sufficiently match one of the stored gesture patterns. If so, then the wearable device assesses whether detection of the matched gesture pattern results in completion of a multi-stage gesture. If the detected matched gesture is the first gesture detected during this process 300, then the multi-stage gesture is not complete. The multi-stage gesture may feature two or more prescribed gestures. If the multi-stage gesture is not complete, then the process 300 may return to operation 302 to evaluate whether a subsequent gesture is detected. If, in operation 310, the wearable device determines that the detected gesture results in completion of the multi-stage gesture, then it sets the hygiene status to "clean" in operation 312.

In some implementations, the wearable device may determine that the multi-stage gesture is complete if all prescribed gestures are detected. In some implementations, the multi-stage gesture may be determined to be complete on the basis that n of m gestures are complete. For example, the policy set in the wearable device may prescribe that 3 of 4 gestures must be detected, or 4 of 6 gestures must be detected. In some cases, the multi-stage gesture may include alpha gestures that must be performed/detected and beta gestures that may be performed/detected. In such an example, the multi-stage gesture may be considered complete only if all the alpha gestures are detected and at least some subset of the beta gestures are detected. For example, if there are six handwashing gestures, two may be alpha gestures and four may be beta gestures. In an example implementation, the wearable device may have a policy set that identifies a valid handwashing event if at least four gestures are completed, where two of those gestures must be the two alpha gestures. As will be described below, the wearable device may require certain minimum durations for the gesture(s) in order to determine that the multi-stage gesture is complete.

The order of the gestures may or may not be a factor in determining whether the multi-stage gesture has been completed. That is, in some cases, the order in which gestures are performed and detected is not germane to determining whether the multi-stage gesture is complete. In some other cases, a policy may be set mandating that one or more of the gestures be detected prior to or after one or more of the other gestures. That is, the multi-gesture protocol may have a prescribed order of at least two of the gestures to constitute a validly performed multi-gesture hygiene event.

Figure 4:
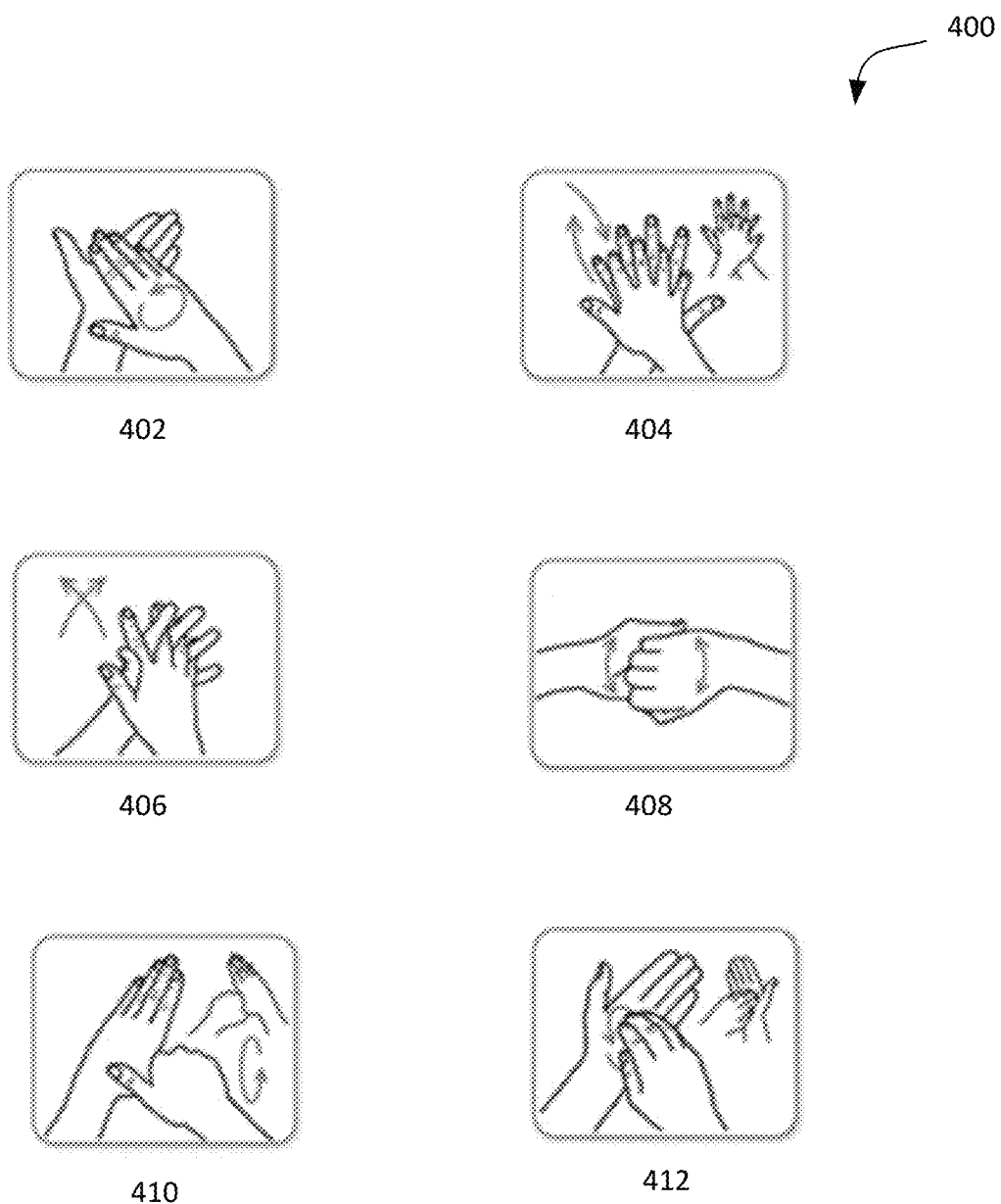
FIG. 4 depicts example gestures in a multi-stage handwashing protocol.

Reference is now made to FIG. 4, which diagrammatically illustrate a multi-stage hygiene gesture. In this example, the multi-stage hygiene gesture is a multi-step handwashing protocol 400. The multi-stage handwashing protocol 400 in this example includes six gestures, as indicated by reference numerals 402, 404, 406, 408, 410, and 412.

The first gesture 402 may involve circular motions in a palm-to-palm configuration. The second gesture 404 may involve right palm over the back of the left hand and a reciprocating motion with fingers laced, and vice versa. The third gesture 406 may involve palm-to-palm reciprocating motion with fingers laced. The fourth gesture 408 may include fingers curled and backs of fingers to opposite palm with twisting reciprocation. The fifth gesture 410 may involves encircling the thumb of the opposite hand and performing circular motions. The sixth gesture 412 may circular motions by one hand having its fingertips pressed into the palm of the other hand.

In any given implementation, an administrative policy may establish which gestures are included, which are necessary, which are optional, any minimum time associated with a particular gesture, and a minimum total time associated with the multi-stage gesture.

Figure 5:
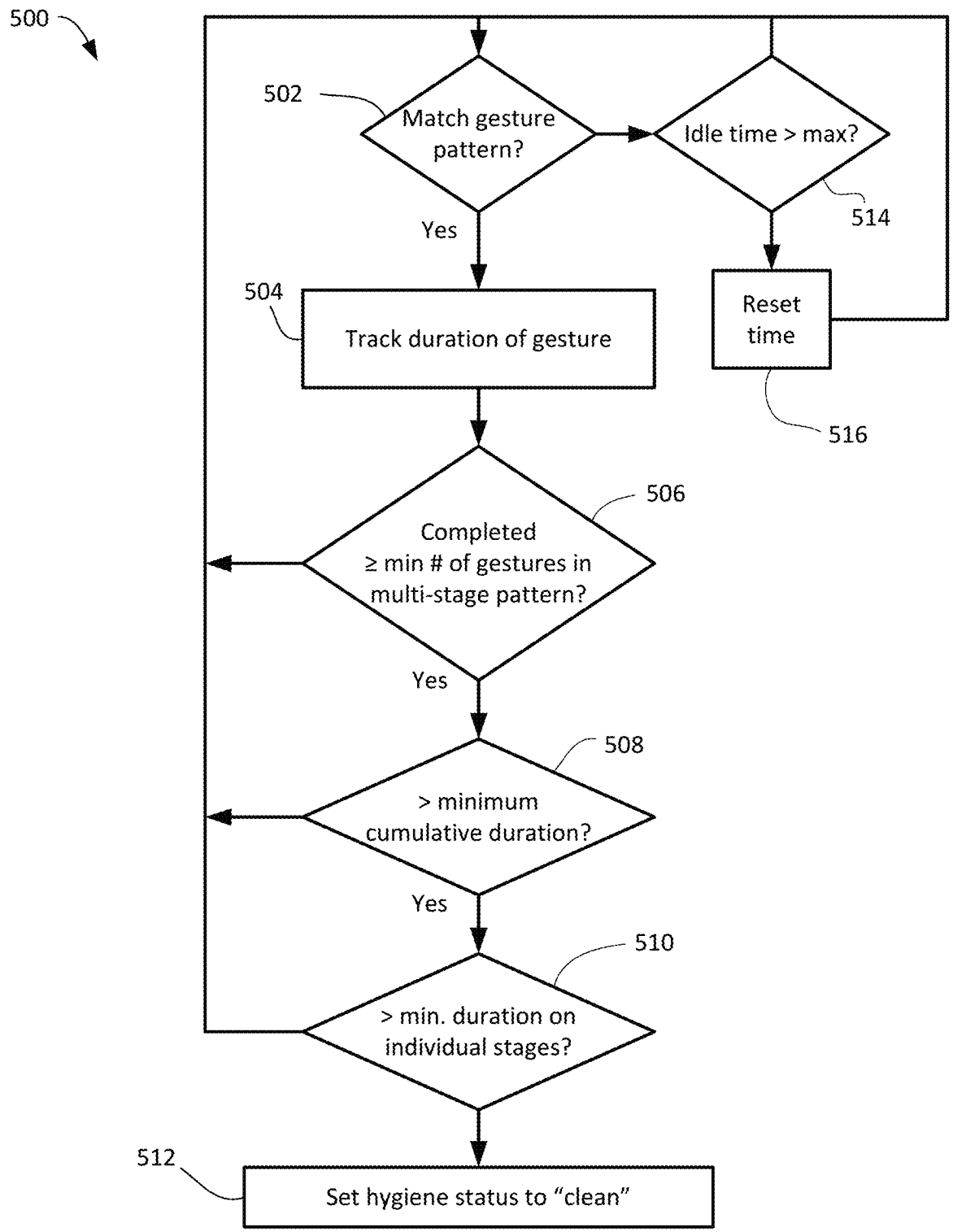
FIG. 5 is a flowchart showing a method of determining completion of a multi-stage hygiene event.

Reference will now be made to FIG. 5 which shows, in flowchart form, an example process 500 for detecting a valid multi-stage hygiene event. The process 500 may be incorporated into the various gesture detection operations of method 200 (FIG. 2), in some examples.

In operation 502, the wearable device determines whether a match is found between an inertial sensor signal(s) and stored gesture signal patterns. If a match is found, in then in operation 504, the wearable device tracks the duration of the gesture. That is, it may record a time duration over which the gesture is detected. In one example, the time duration may be tracked by recording a start timestamp upon detection of the gesture and recording an end timestamp upon determining that the received gesture signal(s) no longer sufficiently match the stored gesture signal pattern identified in operation 502. The time duration for the gesture may be determined as the difference between the recorded end timestamp and the recorded start timestamp.

In operation 506, the wearable device determines whether the detected gesture in operation 502 and 504 results in completion of the requisite number of distinct gestures in the multi-stage hygiene event. As noted above, dependent on an implementation and a specific policy applied by the wearable device, the requisite number may include all prescribed gestures, a subset of the prescribed gestures, or certain required alpha gestures and a subset of the beta gestures. If the requisite gesture have been detected then, in this example, the wearable device determines whether the cumulative duration of the detected gestures exceeds the minimum total duration prescribed by the applicable hygiene policy in the wearable device, as shown in operation 508. That is, the respective durations tracked for each detected gestures in the multi-stage gesture are summed and the total is compared to the minimum total duration. As an example, in the case of a handwashing gestures, the policy may prescribe a minimum total handwashing time of 45 seconds. If the policy also prescribes that at least four of six gestures are performed, then the wearable device assesses in operation 506 whether at least four of six gestures were detected. If so, then in operation 508 the wearable device sums the duration tracked for each detected gesture in the handwashing operation to determine whether the total duration of the detected gestures is at least 45 seconds.

In this example, in operation 510, the wearable device may further determine whether the duration of one or more of the gestures meets or exceeds a respective minimum duration prescribed for that gesture. For example, again in the context of handwashing, one or more of the gestures may have a minimum time associated with it. For example, the hygiene policy set in the wearable device may prescribe that a specific gestures, such as operation 404 (FIG. 4), be performed for at least 10 seconds, and that the overall total duration of the gestures is to be at least 60 seconds. Other policies in other implementations may set minimum durations for none, one, or each of the gestures in a multi-stage gesture.

If the minimum durations (if any) are met in operations 508 and 510, then in operation 512 the hygiene status is set to "clean". Otherwise, the process 500 returns to operation 502 to monitor for other or additional gestures.

While monitoring for gestures, the wearable device may, in this example, determine whether an idle time since detection of the last gesture has exceeded a maximum idle time, as indicated by operation 514. If so, then the wearable device may "reset" the process 500 in operation 516, effectively discarding the gestures detected and tracked in connection with the incomplete multi-stage gesture before returning to operation 502. In other words, if a multi-stage gesture is interrupted for too long such that a further gesture within the multi-stage gesture is not detected within the maximum idle time, then the multi-stage gesture is considered abandoned and incomplete. Subsequent detections of a gesture would then be considered the initial gesture of a new multi-stage gesture hygiene event. In this sense, "idle" time is not intended to indicate that no movement of the wearable device occurs or is detected, but instead that none of the movements of the wearable device during that time matches to a stored gesture signal pattern.

In some cases, the "reset" operation 516 may further be triggered by one or more specific gestures, as will be described below in connection with detection of "unclean" gestures. Such gestures may be considered as interruptions or 'spoilage' of the partially completed multi-stage gestures that mandates discarding of gestures relating to that incomplete multi-stage gesture.

Figure 6:
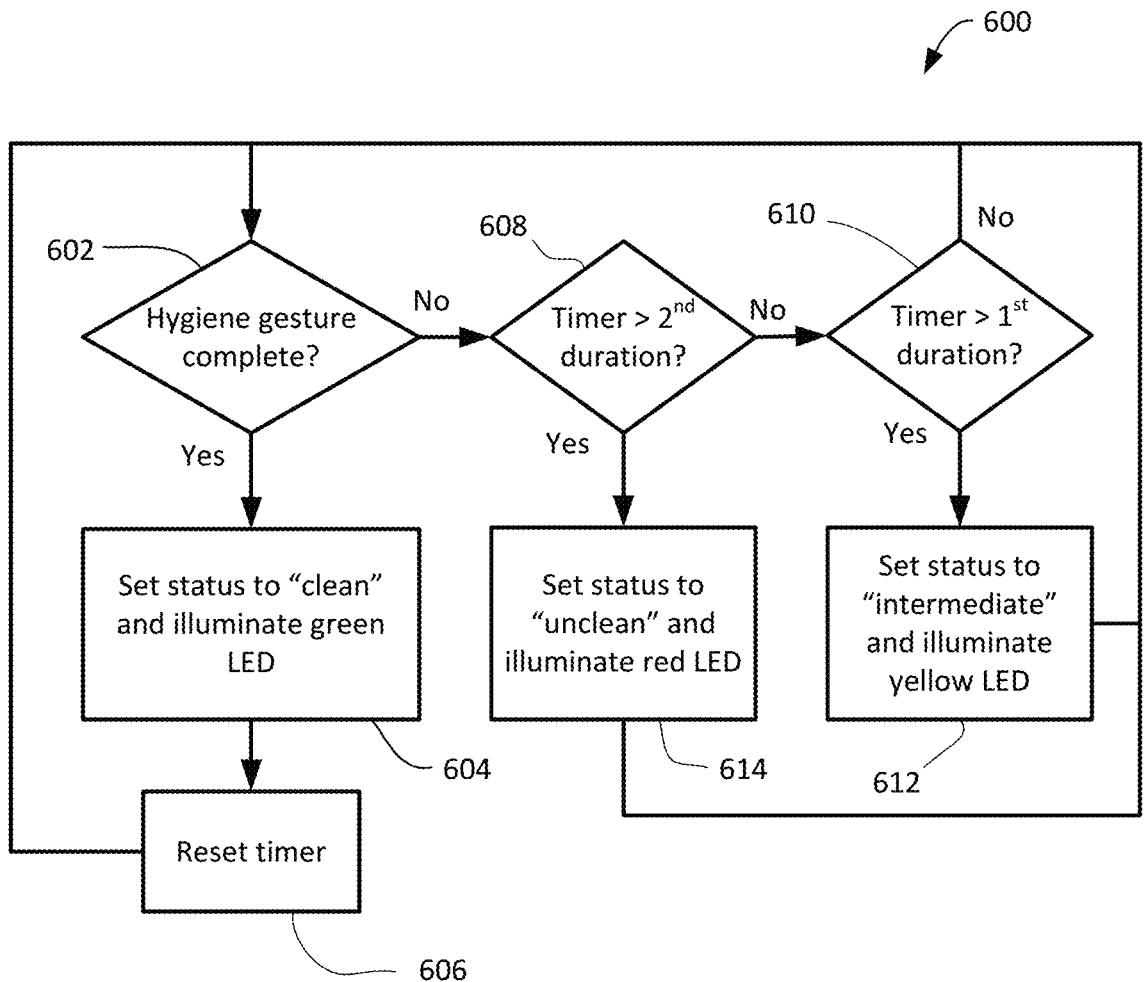
FIG. 6 is a flowchart showing an example method of indicating hygiene status.

A further example process 600 is shown in flowchart form in FIG. 6. The example process 600 illustrates one example method of indicating hygiene status by a wearable device. In this example, the wearable device includes a visual output device, such as display screen, multicolour LED, or multiple LEDs having different colours. In this specific example, the visual output device is capable of at least green illumination, red illumination and yellow illumination. Those specific colours, or the use of three colours, are examples and may be varied in other example implementations.

In operation 602, the wearable device determines that a hygiene event is complete based on detection of a multi-stage gesture. Various methods may be used to determine whether a hygiene event is complete, such as one or more of the example methods described herein. When the hygiene event is detected, the wearable device then causes its output device to output a green indicator in operation 604. For example, a green LED is illuminated. The wearable device further set the hygiene status to "clean". A timer is then initiated or reset in operation 606. The time tracks the time elapsed since detection of the most recent hygiene event. In various examples, the hygiene event may be detection of a handwashing sequence of gestures.

As the wearable device continues to monitor for detecting of a valid hygiene event, it determines whether the timer has reached an expiry time, as indicated by operation 608. The expiry time is a predetermined duration time since the most recent hygiene event. If the expiry time has not been reached, then in operation 610 the wearable device determines whether the timer has reached an intermediate time. The intermediate time is a shorter duration of time than the expiry time. It may be considered a "warning" time or point, as which the wearable device cautions the wearer that a hygiene event will need to be performed soon to prevent the timer from reaching the expiry time.

If the timer has reached the intermediate time, then in operation 612 the wearable device causes its output device to output a yellow indicator. In some examples, this includes illuminating a yellow LED. The hygiene status may also be set to "intermediate" or some equivalent.

If the time reaches the expiry time, as determined in operation 608, then the wearable device causes its output device to output a red indicator in operation 614. In some examples, this include illuminating a red LED. The hygiene status may also be set to "unclean".

It will be appreciated that the wearable device may output other indicators of the change in hygiene status, such as an auditory alert or a haptic vibration alert or wireless notifications to a paired device. It will also be appreciated that in some embodiments there may be no intermediate status or indicator, or there may be additional stages/statuses and indicators with corresponding time durations.

The expiry time and the intermediate time may be pre-set values stored in the device during an initial provisioning operation. In some cases, the expiry time and intermediate time may be set by an administrator policy, which may be set in initial provisioning of the device and/or pushed to the device in a policy update operation over a wired or wireless connection to the device. In some cases, the times may be user configurable and may be modified by the user, provided the user has sufficient credentials to alter the times. The modification of the times may be by way of user input devices in the wearable device itself in some cases, or through use of a corresponding mobile app, website, or other interface on an external device in communication with the wearable device over a wired or wireless connection.

Figure 7:
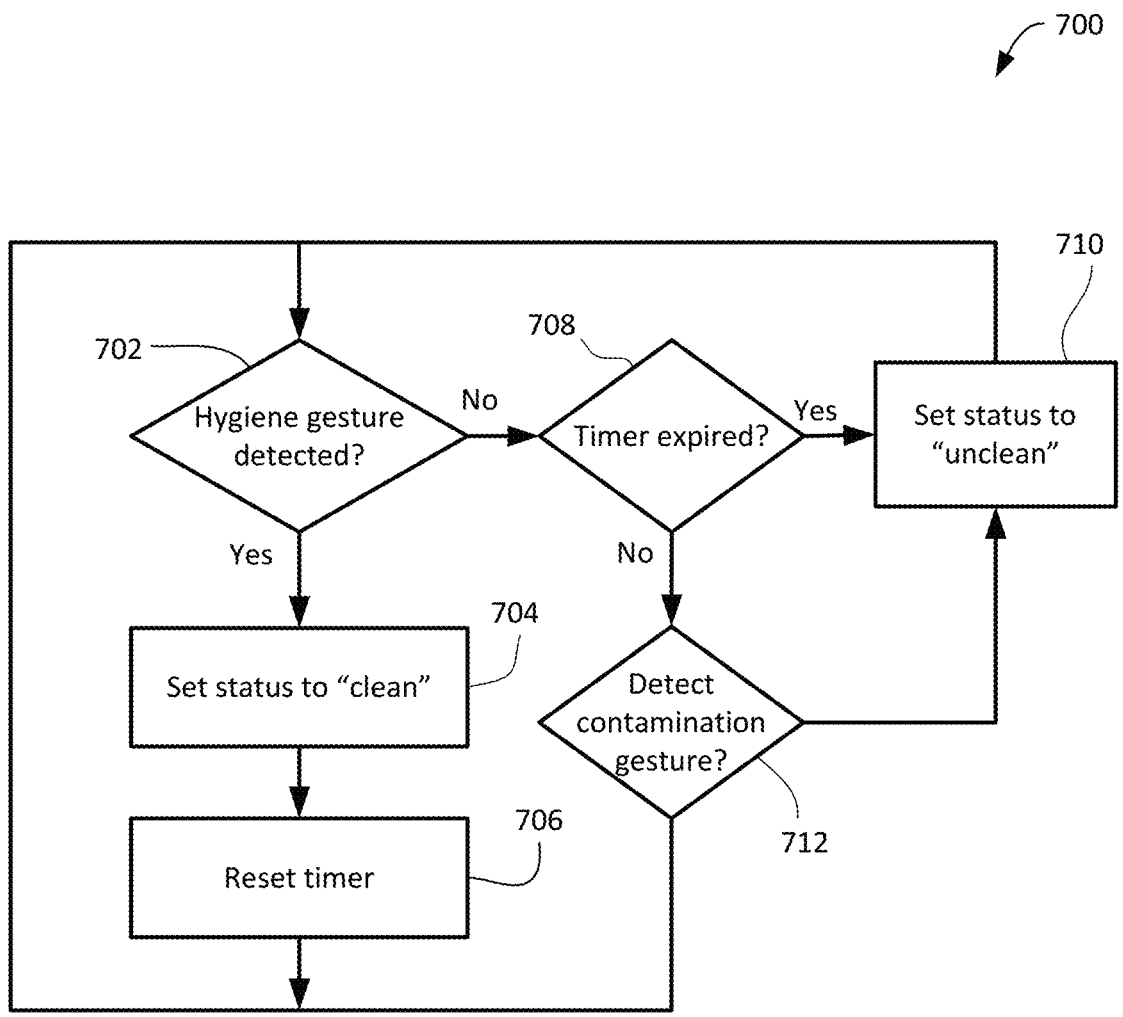
FIG. 7 is a flowchart showing an example method of determining hygiene status based on detecting contamination gestures.

Reference will now also be made to FIG. 7, which shows a simplified example method 700 for changing hygiene status using a wearable device. The example method 700 may be implemented using a wearable device that stores one or more hygiene gesture signals patterns and at least one contamination gesture signal pattern. In operation 702, the wearable device may detect a valid hygiene gesture and, as a result set the device status to "clean" in operation 704 and start a timer in operation 706.

As described above, the wearable device may then monitor for further gestures and for expiry of the timer. As indicated by operation 708, if the timer reaches an expiry time, then in operation 710 the wearable device will set the device status to "unclean". As described in connection with other illustrative embodiments, various output devices may be used to signal current status and/or status changes.

The wearable device in this example also monitors for "contamination" gestures. These are gesture patterns that correspond to a gesture that will result in a need to re-sanitize. For example, one contamination gesture may include a wearer touching his or her face. In the case of a wristband or bracelet, this gesture pattern may correspond to raising the wrist up in close proximity to the wearer's face. In some cases, the wearable device may track or identify a rest point for the wearer's wrist that indicates the hand at a side (subject to small movements when walking, etc.), e.g. a 0-0-0 axis point. Detection of a face touch gesture may, partly, be based on detecting the wearable device at more than a threshold distance above the 0-0-0 point that indicate raising a hand above that threshold distance. In some cases, this threshold may be combined with gyroscope and/or accelerometer data indicating the positional orientation of the hand/wrist and estimated proximity to the wearer's head.

Another "contamination" gesture or event may be coughing or sneezing. Detection of some contamination gestures, such as coughing or sneezing, may rely on microphone input signal matching alone or in combination with inertial signal matching for corresponding gestures. Other gestures may also be considered "contamination" gestures. If such a gesture is detected in operation 712, the device sets its status to "unclean" even if the timer has not expired.

Figure 8:
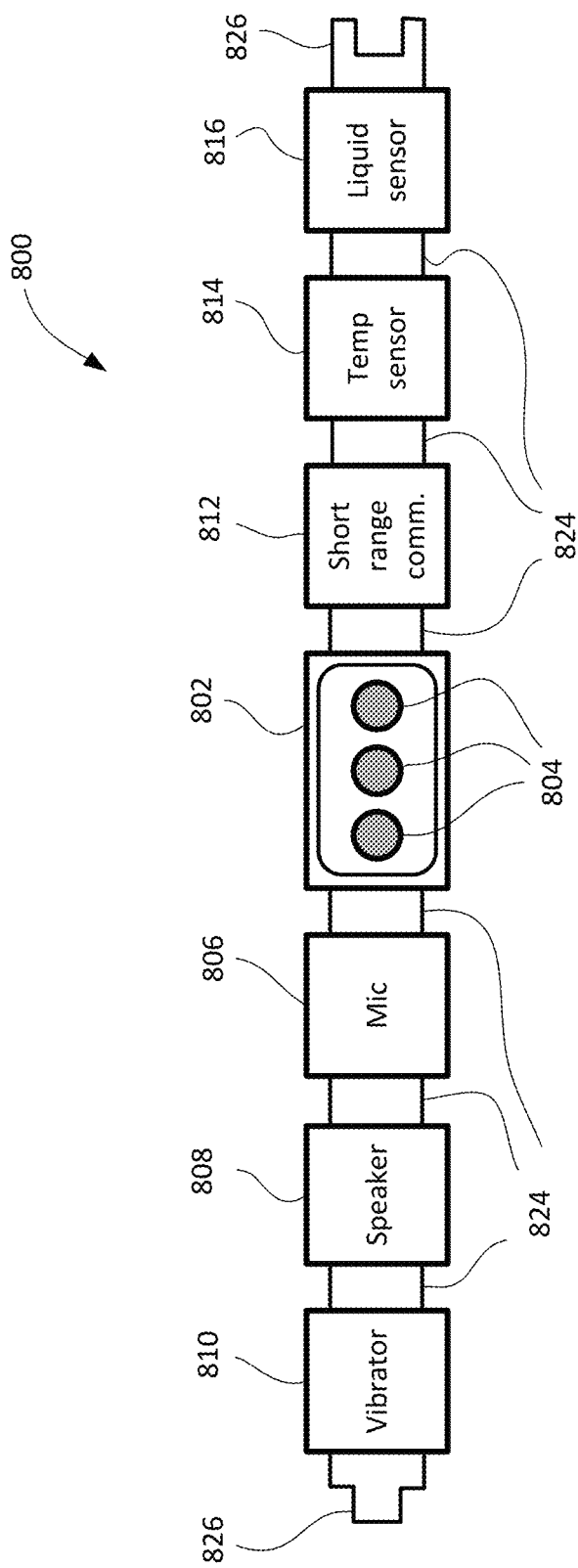
FIG. 8 diagrammatically illustrates an example wearable device for tracking and indicating hygiene status.

Reference will now be made to FIG. 8, which diagrammatically illustrates an example wearable device 800 for tracking and indicating hygiene status. In this example, the wearable device 800 is a bracelet or wristband.

The wearable device 800 may include a main unit 802 that houses at least a processor, memory, a communication subsystem, battery, charge circuitry, and other circuitry for interconnecting components of the wearable device 800 and sending/receiving signals between components. Various other electronic components may be housed within the main unit 802.

The wearable device 800 includes at least one inertial sensor in communication with the processor. The at least one inertial sensor may be housed within the main unit 802.

The main unit 802 may further include a visual output device, such as, in this example, three LEDs 804 for signalling hygiene status using red, yellow, and green colours.

In this example embodiment, the wearable device 800 may be a modular device in which various optional additional physical modules 806-822 may be incorporated into the wearable device 800. Each module may be connected to adjacent modules or to the main unit using connectors 824. The connectors 824 may provide a flexible physical connection between modules, permitting at least some flexion to permit the wearable device 800 to encircle a wrist for example. The connectors 824 may further provide electrical connections coupling each module to the main unit 802 and, in particular, to the processor. In one example, the connectors 824 may connect the modules serially and provide a continuous data bus for exchange of signals. In an alternative implementation, the connectors 824 are implemented as a continuous band incorporating the main unit 802 and onto which modules may be attached. The wearable device 800 may include coupling connectors 826 at either end to permit the wearable device 800 to be detachably secured to a wearer's wrist, for example.

Example modules may include a microphone module 806. The microphone module 806 may include a microphone for receiving audio input and providing corresponding audio signals to the processor. In some implementations, the microphone module 806 may be used to receive voice commands that may cause the processor to take various actions, for example changing settings or configurations. In some implementations, the microphone module 806 may be used in detecting hygiene events. For example, the wearable device 800 may be configured to determine whether a hygiene event is valid based on both gesture detection and audio detection. As an example, in the case of handwashing, audio signals from the microphone module may be used by the processor to detect the sound of running water, or the sound of a hand-sanitizer dispenser prior to detection of the handwashing gestures. For such a purpose, audio signal patterns corresponding to hygiene sounds, such as running water, may be stored in memory on the device and used to determine whether such sounds have been detected. In some implementations, the microphone module 806 may be used, alone or together with the inertial sensor, to identify contamination events, such as a cough or sneeze event.

Another example module may include a speaker module 808. The speaker module 808 may be used to output audio. Example audio may include audio alerts relating to the hygiene status of the device. For instance, the wearable device 800 may output a warning sound upon changing hygiene status from clean to intermediate, or from intermediate to unclean. The wearable device 800 may output a success sound upon detecting a valid hygiene event or upon changing status to clean.

A further example module may include a vibrator module 810. The vibrator module may be used to give haptic feedback to the wearer. The haptic feedback may relate to the hygiene status of the device. For instance, the wearable device 800 may use vibration to signal a change in hygiene status or to signal detection of a valid hygiene event.

Yet another example module may be a short-range communication module 812. The short-range communication module 812 may permit wireless communication with nearby devices. Example protocols for short-range communication include WiFi (e.g. one or more of the IEEE 802.11 protocols), Bluetooth™, NFC, or others. Using Bluetooth™ as an example, the wearable device 800 may be paired with an external device, such as a laptop or mobile smartphone, which may enable the wearer to configure the wearable device using a corresponding application or web interface to send and receive data and configuration instructions with the wearable device 800 via the external device. The wearable device 800 may send hygiene data or reports to the external device on request or on a periodic basis. The reports may include data regarding the detection of hygiene events, timing, portion of time in various hygiene states, signal pattern data, or any other data detected or determined by the wearable device 800. In a corporate or institutional setting, such as a hospital, this may permit the centralization of hygiene tracking data at a server and analysis of that data to identify trends or problems in hygiene activities, or to identify a wearer that is in violation of hygiene policy or in need of corrective instruction.

In one example, the short-range communication module 812 may be configured for wireless communication with a second wearable device (not shown). In the example of a wristwatch or wristband, the second wearable device may be a "sister" device to be worn on the wearer's other arm. One example use case involves having a main wearable device on one wrist and a paired sister wearable device on the other wrist. The paired wearable device may be the same as the main wearable device or may have fewer components and features. For example, the sister device may have a battery, processor, memory, short-range communication subsystem, and inertial sensor, but may not perform gesture identification or have input or output devices. Such a sister device may wirelessly send gesture signal data to the main wearable device for analysis and detection of gestures. By obtaining inertial signal data from both wrists, the main wearable device may be better able to detect hygiene events, such as handwashing, that involve movements by both hands. The gesture signal patterns in such cases may include a left hand pattern and corresponding right hand pattern for each gesture. The matching of inertial signals to patterns may require that the obtained signals are at least a threshold match to both the left hand and right hand patterns of the same gesture to be identified as a valid gesture detection.

Another example module may be a temperature sensor 814. In some examples, the temperature sensor 814 may be used to aid in determining whether a valid hygiene event has occurred. As an example, in some cases a policy may be set in which a valid handwash may require water of at least a minimum temperature, and the temperature sensor 814 may provide a signal to the processor to enable the processor to determine whether the water used in a handwash event was of a sufficient temperature. In some cases, the temperature sensor 814, may be used for sensing ambient temperature and making corresponding adjustments to the expiry time and/or intermediate time or other such parameters. For instance, a policy may be applied in which warmer temperatures or temperatures above a certain level cause the device 800 to shorten the expiry time in the expectation that more frequent sanitization may be required due to more significant perspiration or greater survivability for pathogens. Other policies may be used to make other adjustments based on temperature.

A further example module may be a liquid sensor 816. The liquid sensor 816 may be configured to sense water for determining whether a valid handwashing gesture is detected. The liquid sensor 816 may include a chemical sensor configured to detect soaps in some cases. In some cases, the chemical sensor may be configured to sense alcohol. That data may be used by the wearable device in determining whether a valid handwashing gesture has been detected. In some cases, the liquid sensor 816 may be configured to determine a soap concentration or an alcohol concentration for determining whether sufficient soap and/or hand-sanitizer has been employed in the handwashing event.

Other modules may be incorporated in the wearable device 800, including module relating to detecting health status of the wearer, air quality of the environment, activity levels of the wearer, etc. The wearable device 800 may also include a communications port, such as a mini-USB port or the like, through which charging current may be supplied and/or communications with external devices established. In some cases, the communications port and/or the short-range communications module 812 may permit firmware updates, application updates, and other software maintenance operations for the wearable device 800.

Implementations

The methods and devices described herein may be deployed in part or in whole using a processor that executes computer software, program codes, and/or instructions. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods, program codes, and instructions described herein may be implemented in different devices which may operate in wired or wireless networks. Examples of wireless networks include 4th Generation (4G) networks (e.g. Long Term Evolution (LTE)) or 5th Generation (5G) networks, as well as non-cellular networks such as Wireless Local Area Networks (WLANs). However, the principles described herein may equally apply to other types of networks.

The computer software, program codes, and/or instructions described herein may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another, such as from usage data to a normalized usage dataset.

The elements described and depicted herein, including in flowcharts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Furthermore, the elements depicted in the flowcharts and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above, and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

The invention claimed is:

1. A method of indicating a hygiene status on a wearable device, the method comprising:
    obtaining a first gesture signal using an inertial sensor in the wearable device;
    matching the first gesture signal to one of a plurality of gesture signal patterns stored in the wearable device and associated with a multi-stage gesture by determining that the first gesture signal differs from said one of the plurality of gesture signal patterns by less than a threshold amount;
    obtaining at least one more gesture signal using the inertial sensor;
    matching the at least one more gesture signal to respective other ones of the plurality of gesture signal patterns;
    determining, based on matching the first gesture signal to the one of the plurality of gesture signal patterns plus matching the at least one more gesture signal to respective other ones of the plurality of gesture signal patterns that the multi-stage gesture has been completed and, as a result, setting the hygiene status to a clean state; and outputting a sensory signal using an output device indicating the clean state.

2. The method of claim 1, wherein determining is further based on determining that the first gesture signal and the at least one more gesture signal do not match an excluded gesture pattern.

3. The method of claim 1, wherein determining that the multi-stage gesture has been completed is further based on determining that a cumulative duration of the first gesture signal and the at least one more gesture signal is greater than a minimum total duration value.

4. The method of claim 1, wherein the first gesture signal and each gesture signal in the at least one more gesture signal are respective gesture signals, and wherein determining that the multi-stage gesture has been completed is further based on determining that a respective elapsed duration of each of the respective gesture signals is greater than a respective minimum duration associated with that respective gesture signal.

5. The method of claim 1, wherein the threshold amount is based on a standard deviation measurement associated with said one of the plurality of gesture signal patterns and stored on the wearable device.

6. The method of claim 1, wherein the multi-stage gesture includes at least six gestures, the first gesture signal and each gesture signal in the at least one more gesture signal are respective gesture signals, and wherein the matching the first gesture and the matching the at least one more gesture signal include matching respective ones of the respective gesture signals to each of the at least six gestures.

7. The method of claim 1, further comprising:
detecting that an elapsed time since the setting the hygiene status to the clean state exceeds an expiry time and, as a result, setting the hygiene status to unclean; and
outputting a signal to indicate the unclean hygiene status.

8. The method of claim 7, further comprising:
prior to detecting that the elapsed time exceeds the expiry time, detecting that the elapsed time exceeds an intermediate time shorter than the expiry time and, as a result, setting the hygiene status to intermediate; and
outputting a signal to indicate the intermediate hygiene status.

9. The method of claim 8, wherein the sensory signal indicating the clean status includes a green output, the signal to indicate the intermediate hygiene status includes a yellow output, and signal to indicate the unclean hygiene status includes a red output.

10. The method of claim 9, wherein the output device includes one or more light-emitting diodes on an external surface of the wearable device, and wherein the green output includes illuminating the one or more light-emitting diodes green, the yellow output includes illuminating the one or more light-emitting diodes yellow, and the red output includes illuminating the one or more light-emitting diodes red.

11. The method of claim 1, further comprising, subsequent to the setting of the hygiene status to clean, obtaining a new gesture signal and matching the new gesture signal to a reset gesture pattern and, as a result, setting the hygiene status to unclean and outputting a signal indicating the unclean hygiene status.

12. The method of claim 1, wherein the output device includes one or more of a light-emitting diode, a display screen, a speaker, or a vibrator.

13. The method of claim 1, further comprising receiving a wireless signal from a paired wearable device, the wireless signal including at least one gesture signal obtained by the paired wearable device, and wherein determining further includes matching the at least one gesture signal to a particular one of the plurality of gesture signal patterns.

14. The method of claim 13, wherein the at least one gesture signal is obtained by the paired wearable device during a time period in which the wearable device obtains the first gesture signal; and wherein said one of the plurality of gesture signal patterns matched to the first gesture is paired with said particular one of the plurality of gesture signal patterns matched to the at least one gesture signal.

15. A wearable device to indicate a hygiene status, the device comprising:
a memory storing a plurality of gesture signal patterns associated with a multi-stage gesture;
an inertial sensor to output gesture signals representative of movement of the device;
a processor; and
an output device,
wherein the memory includes processor-executable instructions that, when executed by the processor, are to cause the processor to:
receive a first gesture signal from the inertial sensor;
match the first gesture signal to one of the plurality of gesture signal patterns by determining that the first gesture signal differs from said one of the plurality of gesture signal patterns by less than a threshold amount;
receive at least one more gesture signal from the inertial sensor;
match the at least one more gesture signal to respective other ones of the plurality of gesture signal patterns;
determine, based on matching the first gesture signal to the one of the plurality of gesture signal patterns plus matching the at least one more gesture signal to respective other ones of the plurality of gesture signal patterns that the multi-stage gesture has been completed and, as a result, set the hygiene status to a clean state; and
cause the output device to output a sensory signal indicating the clean state.

16. The wearable device of claim 15, wherein the wearable device is one of a bracelet, armband, wristband, wristwatch, or ring.

17. The wearable device of claim 15, wherein the instructions, when executed, are to further cause the processor to determine that the multi-stage gesture has been completed by further determining that a cumulative duration of the first gesture signal and the at least one more gesture signal is greater than a minimum total duration value.

18. The wearable device of claim 15, wherein the first gesture signal and each gesture signal in the at least one more gesture signal are respective gesture signals, and wherein the instructions, when executed, are to further cause the processor to determine that the multi-stage gesture has been completed by further determining that a respective elapsed duration of each of the respective gesture signals is greater than a respective minimum duration associated with that respective gesture signal.

19. The wearable device of claim 15, wherein the instructions, when executed, are to further cause the processor to detect that an elapsed time since the setting the hygiene status to the clean state exceeds an expiry time and, as a result, to set the hygiene status to unclean; and to cause the output device to output a signal to indicate the unclean hygiene status.

20. A wearable device to indicate a hygiene status, the device comprising:
   a memory storing a plurality of gesture signal patterns associated with a multi-stage gesture;
   an inertial sensor to output gesture signals representative of movement of the device;
   a processor; and
   an output device,
   wherein the memory includes processor-executable instructions that, when executed by the processor, are to cause the processor to:
      receive a first gesture signal from the inertial sensor;
      match the first gesture signal to one of the plurality of gesture signal patterns;
      receive at least one more gesture signal from the inertial sensor;
      match the at least one more gesture signal to respective other ones of the plurality of gesture signal patterns;
      determine, based on matching the first gesture signal to the one of the plurality of gesture signal patterns plus matching the at least one more gesture signal to respective other ones of the plurality of gesture signal patterns that the multi-stage gesture has been completed and, as a result, set the hygiene status to a clean state;
   cause the output device to output a sensory signal indicating the clean state; and
   subsequent to the setting of the hygiene status to clean, obtain a new gesture signal and match the new gesture signal to a reset gesture pattern and, as a result, set the hygiene status to unclean and output a signal indicating the unclean hygiene status.

* * * * *